US 7,314,599 B2

(12) United States Patent
Roitman et al.

(10) Patent No.: US 7,314,599 B2
(45) Date of Patent: Jan. 1, 2008

(54) PAEK EMBOSSING AND ADHESION FOR MICROFLUIDIC DEVICES

(75) Inventors: Daniel B. Roitman, Menlo Park, CA (US); Kevin P. Killeen, Palo Alto, CA (US); Karen L. Seaward, Palo Alto, CA (US); Hongfeng Yin, San Jose, CA (US); Karla Robotti, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 977 days.

(21) Appl. No.: 10/114,801

(22) Filed: Apr. 2, 2002

(65) Prior Publication Data

US 2003/0017305 A1 Jan. 23, 2003

Related U.S. Application Data

(63) Continuation-in-part of application No. 09/908,231, filed on Jul. 17, 2001.

(51) Int. Cl.
*B32B 27/04* (2006.01)
(52) U.S. Cl. ...................... 422/102; 156/209
(58) Field of Classification Search ............... 156/292, 156/309.3, 309.6, 209, 272.6, 308.2, 4, 6; 422/102
See application file for complete search history.

(56) References Cited

U.S. PATENT DOCUMENTS 4,775,587 A * 10/1988 Walles ...................... 428/305.5
5,888,609 A * 3/1999 Karttunen et al. ........... 428/107
6,267,884 B1 7/2001 Myers
6,653,124 B1 * 11/2003 Freeman ................... 435/297.1
2002/0176804 A1* 11/2002 Strand et al. ............... 422/100
2002/0191990 A1* 12/2002 Hirano et al. ............... 399/279

FOREIGN PATENT DOCUMENTS

| DE | 19922075 | 11/2000 |
| DE | 10036976 A1 | 3/2001 |
| EP | 0856400 A1 | 8/1998 |
| JP | 009067558 | 3/1997 |
| WO | WO 01/87458 | 11/2001 |

OTHER PUBLICATIONS

F.J. Medellin-Rodriguez and P.J. Phillips; "*Poly(ARYL Ether Ether Ketone) [PEEK] (Bulk Crystallization Kinetics)*"; Polymeric Material Encycolpedia, J:Salamone, Ed., CRC Press New York, 1996; pp. 5513-5591.
Westlake Plastics Company; "*PEEK™ Film (polyetheretherketone)*"; Aug. 2001; pp. 1-2.

* cited by examiner

*Primary Examiner*—Jill Warden
*Assistant Examiner*—Natalia Levkovich

(57) ABSTRACT

A fabrication and adhesion method for a polyaryl-ether-ketone (PAEK) device, such as a microfluidic device, is disclosed. At least one glassy uncrystallized PAEK substrate is heated up to near or above the glass transition temperature to allow the substrate to crystallize from the glass state, while embossing the substrate with patterns. Bonding the PAEK substrate to another substrate is accomplished using a solvent-resistant adhesive, such as a polyimide-based adhesive, in combination with an adhesion enhancement treatment. In certain embodiments, the adhesion enhancement treatment is a plasma treatment or a chemical sulfonation treatment.

13 Claims, 9 Drawing Sheets

PAEK EMBOSSING AND ADHESION FOR MICROFLUIDIC DEVICES

CROSS-REFERENCE TO RELATED APPLICATIONS

This U.S. Nonprovisional Application for Patent is a Continuation-in-Part of U.S. Nonprovisional Application for Patent Ser. No. 09/908,231, which was filed on Jul. 17, 2001. U.S. Nonprovisional Application for Patent Ser. No. 09/908,231 is also hereby incorporated by reference in its entirety herein.

BACKGROUND OF THE INVENTION

1. Technical Field of the Invention

The present invention relates generally to microfluidic devices, and particularly to fabrication and adhesion of microfluidic devices.

2. Description of Related Art

In recent years, microfluidic device technologies, also referred to as microfluidics and Lab-on-a-Chip technologies, have been proposed for a number of applications, including chemical analysis for pharma, biotechnology, fuel cells, etc. Microfluidic devices hold great promise for many applications, particularly in applications that employ rare or expensive fluids, such as proteomics and genomics. The small size of the microfluidic devices allows for the analysis of minute quantities of sample. Having the potential to integrate functions such as sample collection, sample preparation, sample introduction, separation, detection, and compound identification in one device, microfluidic devices such as μ-total analysis systems (μ-TAS) have come to represent the main focus of academic and industrial laboratories research relating to chemical analysis tools or clinical diagnostic tools.

Microfluidic devices having integrated components, e.g., for sample preparation, separation and detection compartments have been proposed in a number of patents. See, e.g., U.S. Pat. No. 5,500,071 to Kaltenbach et al., U.S. Pat. No. 5,571,410 to Swedberg et al., and U.S. Pat. No. 5,645,702 to Witt et al. Because such microfluidic devices have a relatively simple construction, they are in theory inexpensive to manufacture.

Microfluidic devices may be adapted to employ or carry out a number of different separation techniques. Capillary electrophoresis (CE), for example, separates molecules based on differences in the electrophoretic mobility of the molecules. Typically, microfluidic devices employ a controlled application of an electric field to induce fluid flow and or to provide flow switching. In order to effect reproducible and/or high-resolution separation, a fluid sample "plug," a predetermined volume of fluid sample, must be controllably injected into a capillary separation column or conduit. For fluid samples containing high molecular weight charged biomolecular analytes such as DNA fragments and proteins, microfluidic devices containing a capillary electrophoresis separation conduit a few centimeters in length may be effectively used in carrying out sample separation of small volumes of fluid sample having a length on the order of micrometers. Once injected, high sensitivity detection such as laser-induced fluorescence (LIF) may be employed to resolve a separated fluorescently labeled sample component.

For samples containing analyte molecules with low eletrophoretic differences, such as those containing small drug molecules, the separation technology of choice is often based on chromatography. Chromatographic separation occurs when a mobile phase carries sample molecules through a chromatography bed (stationary phase) where sample molecules interact with the stationary phase surface. The velocity at which a particular sample component travels through a chromatography bed depends on the component's partition between mobile phase and stationary phase.

There are many chromatographic techniques known in the art. For example, in reverse phase liquid chromatography, where the stationary phase offers a hydrophobic surface and the mobile phase is usually a mixture of water and organic solvent, the least hydrophobic component moves through the chromatography bed first, followed by other components, in order of increasing hydrophobicity. In other words, the chromatographic separation of sample components may be based on hydrophobicity. In isocratic liquid chromatography, the content of the mobile phase is constant throughout the separation. Gradient liquid chromatography, on the other hand, requires the content of the mobile phase to change during separation. Gradient liquid chromatography not only offers high resolution and high-speed separation of wide ranges of compounds, it also allows injection of large sample volumes without compromising separation efficiency. During the initial period when the sample is introduced, the mobile phase strength is often kept low, and the sample is trapped at the head of the liquid chromatography column bed. As a result, interfering moieties such as salts are washed away. In this regard, gradient liquid chromatography is suited to analyze fluid samples containing a low concentration of analyte moieties.

Such microfluidic devices have typically been fabricated by etching grooves, holes, and other features on the surface of a rigid or flexible substrate. The resulting patterned substrate is capped and bonded with another substrate, forming channels where gases or liquids move to accomplish the various applications the devices are designed for. Conventional rigid substrate materials include silicon, glass, metals. Conventional flexible substrate materials include thermoplastic materials, such as PDMS (polydimethysiloxane) and polyacrylates, thermosets, such as epoxides, and solution-processed polymers, such as polyimides.

Flexible substrate materials are typically preferred to rigid substrate materials due to their lower price and the diversity of processing methods they afford, such as thermoforming, injection molding, etc. Of the available flexible substrate materials, certain polymeric thermoplastic substrate materials have been suggested for use in microfluidic devices due to desirable properties, such as high mechanical modulus, toughness, low thermal distortion and high chemical resistance. For example, such polymeric materials can include polyaryl-ether-ketones (PAEK), such as polyether-ether-ketone (PEEK), polyether-ketone-ether-ketone-ketone (PEKEKK) and polyether-ketone-ketone (PEKK).

For example, U.S. Pat. No. 6,267,884 to Myers (hereinafter referred to as Myers), which is hereby incorporated by reference, discusses using a polymeric substrate material, such as PEEK, to form a capillary liquid chromatography column. The Myers capillary column is formed by molding one plate of the substrate material to produce the capillary column, placing beads within the capillary column and bonding a second plate to the first plate to seal the capillary column.

Although PEEK is mentioned in Myers as a possible substrate material, in practice, PAEK thermoplastic materials have presented difficult manufacturing challenges. One challenge has been that the melt-processing equipment and tools necessary to process PAEK are expensive due to the fact that PAEK is a high-temperature melting engineering thermoplastic. Moreover, the high melting point temperature ($T_m$) of PAEK has also made it difficult to optimize the process conditions.

In addition, traditional bonding materials used for PAEK devices, such as epoxides and acrylates, are not chemically inert to the solvents and temperatures that are commonly required in microfluidic applications, such as High Performance Liquid Chromatography (HPLC). For example, as described in a pamphlet produced on a web page of the Westlake Plastics Company (www.westlakeplastics.com), traditional adhesive agents have included various epoxides and cyanoacrylates. Such traditional adhesive agents are not sufficiently resistant to solvents, such as methyl sulfoxide (DMSO), dimethyl formamide (DMF) and N-methyl pyrrolidone (NMP). Furthermore, PAEK devices have also proved resistant to many of the traditional bonding materials. Therefore, it has been difficult to bond PAEK to PAEK and PAEK to other materials. What is needed is a method of bonding PAEK substrates for use in fabricating microfluidic devices.

SUMMARY OF THE INVENTION

The present invention provides a fabrication and adhesion method for a PAEK device, such as a microfluidic device. At least one uncrystallized glassy (referred to herein as amorphous) PAEK substrate is heated up to near or above the glass transition temperature ($T_g$) to allow for the substrate to crystallize from the glass state, while embossing the substrate with patterns. Bonding the PAEK substrate to another substrate is accomplished using a solvent-resistant adhesive, such as a polyimide-based adhesive, in combination with an adhesion enhancement treatment. In certain embodiments, the adhesion enhancement treatment is a plasma treatment or a chemical sulfonation treatment.

In embodiments of the present invention, the patterns are formed in the PAEK substrate by applying pressure to the PAEK substrate with platens containing a negative pattern with the desired features. In further embodiments, the patterns are formed on one PAEK substrate or two or more PAEK substrates that are bonded together. In other embodiments, the patterned PAEK substrate is bonded to another material, such as glass or other solvent-resistant material. In addition, the polyimide-based adhesive can be applied to two PAEK substrates or to only one PAEK substrate, with the other substrate being a PAEK substrate or any other solvent-resistant material substrate.

In further embodiments, the polyimide-based adhesive layer is thin in comparison to the channel depth of the channels patterned in the PAEK substrate. In one embodiment, the polyimide-based adhesive layer is between 0.1 microns and 1 micron thick. The thickness of the layer of polyimide-based adhesive is controlled by the dilution percentage of the resin concentration of the adhesive formulation (e.g., 10% neat resin in NMP) and by varying the deposition regimes (e.g., spin speed if the resin is spin-coated, drawing rate if the resin is dip-coated, jet-printing conditions, spraying conditions, etc.).

Advantageously, by embossing the PAEK substrates relatively near the PAEK glass transition and crystallization temperatures, the platens can be kept at a narrow temperature range without having to cycle the platens through the PAEK melting point temperature. Another advantage is that the polyimide-based adhesive is chemically inert to many of the solvents and temperatures that are used in microfluidic devices. In addition, the combination of the polyimide-based adhesive and adhesion enhancement treatment applied to the surface of the embossed PAEK substrate enables the PAEK substrate to bond not only to another PAEK substrate, but also to other solvent-resistant materials. Furthermore, the invention provides embodiments with other features and advantages in addition to or in lieu of those discussed above. Many of these features and advantages are apparent from the description below with reference to the following drawings.

BRIEF DESCRIPTION OF THE DRAWINGS

The disclosed invention will be described with reference to the accompanying drawings, which show important sample embodiments of the invention and which are incorporated in the specification hereof by reference, wherein:

FIG. 1A illustrates the device in exploded view. FIGS. 1B and 1C schematically illustrate the microfluidic device in first and second flow path configurations, respectively;

FIG. 2A schematically illustrate the microfluidic device. FIG. 2B illustrate an example of the valve plate that may be employed to effect flow switching between the parallel conduits;

DETAILED DESCRIPTION OF THE EXEMPLARY EMBODIMENTS OF THE INVENTION

Figure 1A:
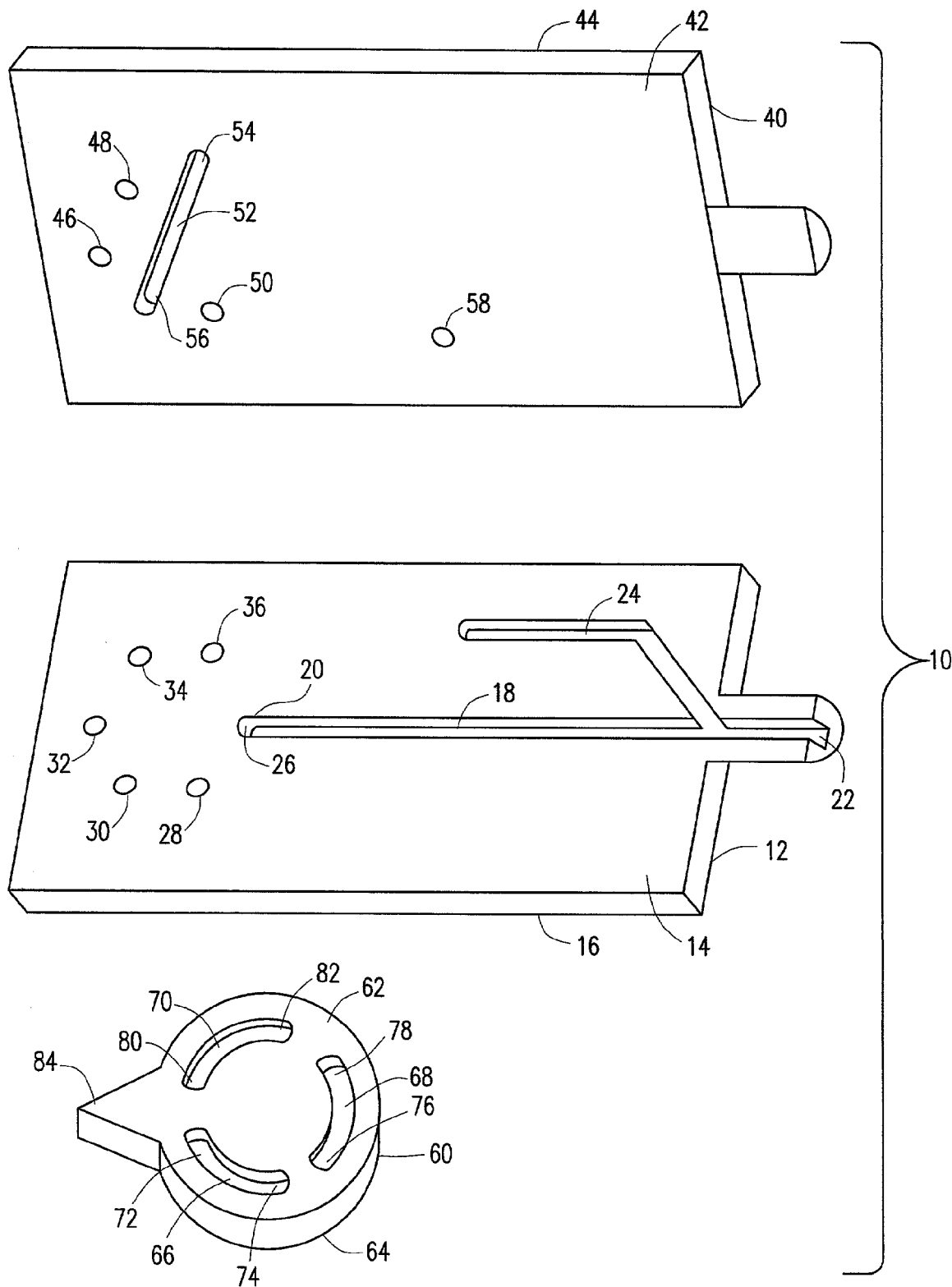
FIGS. 1A-1C, collectively referred to as FIG. 1, illustrates a microfluidic device having an integrated introducing means that employs the rotational sliding motion of a switching plate in order to effect fluid communication between fluid-transporting features.

The numerous innovative teachings of the present application will be described with particular reference to the exemplary embodiments. However, it should be understood that these embodiments provide only a few examples of the many advantageous uses of the innovative teachings herein. In general, statements made in the specification do not necessarily delimit any of the various claimed inventions. Moreover, some statements may apply to some inventive features, but not to others.

It must be noted that, as used in the specification and the appended claims, the singular forms "a," "an" and "the" include plural referents unless the context clearly dictates otherwise. Thus, for example, reference to "a mechanical"

includes a plurality of micro channels, reference to "a fluid" includes a mixture of fluids, reference to "a component property" includes a plurality of component properties and the like.

In this specification and in the claims that follow, reference will be made to a number of terms that shall be defined to have the following meanings:

The term "constructed" as used herein refers to forming, assembling, modifying or combining components in order to build at least a portion of the inventive microfluidic device. Thus, "a conduit constructed for separating" as used herein refers to assembling or combining parts to form a conduit or modifying a surface of a conduit, wherein the conduit serves to differentiate or discriminate sample fluid components. For example, a conduit constructed for separating the components of a fluid sample may have a chemically, mechanically or energetically modified interior surface that interacts with different components differently, or may contain separating media such as chromatographic packing material.

The term "controllably introduced" as used herein refers to the delivery of a predetermined volume of a fluid sample in a precise and accurate manner. A fluid sample may be "controllably introduced" through controllable alignment of two components of a microfluidic device, i.e., fluid-transporting features.

The term "flow path" as used herein refers to the route or course along which a fluid travels or moves. Flow paths are formed from one or more fluid-transporting features of a microfluidic device.

The term "fluid-transporting feature" as used herein refers to an arrangement of solid bodies or portions thereof that direct fluid flow. Fluid-transporting features include, but are not limited to, chambers, reservoirs, conduits and channels. The term "conduit" as used herein refers to a three-dimensional enclosure formed by one or more walls and having an inlet opening and an outlet opening through which fluid may be transported. The term "channel" is used herein to refer to an open groove or a trench in a surface. A channel in combination with a solid piece over the channel forms a conduit.

The term "fluid-tight" is used herein to describe the spatial relationship between two solid surfaces in physical contact such that fluid is prevented from flowing into the interface between the surfaces.

The term "in order" is used herein to refer to a sequence of events. When a fluid travels "in order" through an inlet port and a conduit, the fluid travels through the inlet port before traveling through the conduit. "In order" does not necessarily mean consecutively. For example, a fluid traveling in order through an inlet port and outlet port does not preclude the fluid from traveling through a conduit after traveling through the inlet port and before traveling through the outlet port.

The term "micro alignment means" is defined herein to refer to any means for ensuring the precise micro alignment of micro fabricated features in a microfluidic device. Micro alignment means can be formed either by laser ablation or by other methods of fabricating shaped pieces well known in the art. Representative micro alignment means that can be employed herein include a plurality of appropriately arranged protrusions in component parts, e.g., projections, depressions, grooves, ridges, guides, or the like.

The term "microfluidic device" refers to a device having features of micron or submicron dimensions, and which can be used in any number of chemical processes involving very small amounts of fluid. Such processes include, but are not limited to, electrophoresis (e.g., capillary electrophoresis or CE), chromatography (e.g., µLC), screening and diagnostics (using, e.g., hybridization or other binding means), and chemical and biochemical synthesis (e.g., DNA amplification as may be conducted using the polymerase chain reaction, or "PCR") and analysis (e.g., through enzymatic digestion). The features of the microfluidic devices are adapted to the particular use. For example, microfluidic devices that are used in separation processes, e.g., CE, contain micro channels (termed "micro conduits" herein when enclosed, i.e., when the cover plate is in the place on the micro channel-containing substrate surface) on the order of 1 µm to 200 µm in diameter, typically 10 µm to 75 µm in diameter, and approximately 0.1 to 50 cm in length. Microfluidic devices that are used in chemical and biochemical synthesis, e.g., DNA amplification, will generally contain reaction zones (termed "reaction chambers" herein when enclosed, i.e., again, when the cover plate is in place on the micro channel-containing substrate surface) having a volume of about 1 µl to about 100 µl, typically about 10 µl to 20 µl.

"Optional" or "optionally" as used herein means that the subsequently described feature or structure may or may not be present, or that the subsequent described event or circumstance may or may not occur, and that the description includes instances where a particular feature or structure is present and instances where the feature or structure is absent, or instances where the event or circumstance occurs and instances where it does not.

Thus, the invention generally relates to a microfluidic device for separating the components of a fluid sample. The microfluidic device is constructed from a substrate having first and second opposing surfaces, wherein the substrate has a micro channel formed in the first surface. A cover plate is arranged over the first surface and, in combination with the micro channel, defines a separation conduit for separating the components of the fluid sample according to a component property. A sample inlet port is provided in fluid communication with the conduit to allow a fluid sample introduced from a sample source to be conveyed in a defined sample flow path such that the sample travels, in order, through the sample inlet port, the separation conduit and a sample outlet port. An integrated introducing means is provided for controllably introducing a volume of the fluid sample from a sample source into the sample inlet port. In contrast to previously proposed micro separation devices, which have a motive force means that may fail to provide for adequate control over fluid sample introduction, the integrated introducing means herein provides for improved separation performance in terms of throughput and resolution.

FIG. 1 illustrates a microfluidic device having an integrated introducing means in combination with an integrated separation column for liquid chromatography. As with all figures referenced herein, in which like parts are referenced by like numerals, FIG. 1 is not necessarily to scale, and certain dimensions may be exaggerated for clarity of presentation. The microfluidic device 10 employs a switching structure that employs rotational motion to controllably introduce a predetermined volume of fluid sample. As illustrated in FIG. 1A, the microfluidic device 10 includes a substrate 12 comprising first and second substantially planar opposing surfaces indicated at 14 and 16, respectively, and is comprised of a material that is substantially inert with respect to fluids that will be transported through the microfluidic device. The substrate 12 has a fluid-transporting feature in the form of a sample micro channel 18 in the first planar surface 14. The sample micro channel 18 represents a portion of a separation conduit 25 as discussed below. The fluid-transporting feature may be formed through laser ablation or other techniques discussed below or known in the art. It will be readily appreciated that although the sample micro channel 18 has been represented in a generally extended form, sample micro channels for this and other embodiments can have a variety of configurations, such as a straight, serpentine, spiral, or any tortuous path. Further, as described above, the sample micro channel 18 can be formed in a wide variety of channel geometics, including semi-circular, rectangular, rhomboid, and the like, and the channels can be formed in a wide range of aspect ratios. A device may also have a plurality of sample micro channels. The sample micro channel 18 has a sample inlet terminus 20 at a first end and a sample outlet terminus 22 at the opposing end. As shown in FIG. 1, the sample outlet terminus is located at a protrusion of the otherwise rectangular substrate 12. In addition, an optional make-up fluid micro channel 24 is also formed in the first planar surface 14 in fluid communication with the sample micro channel 18, downstream from the sample inlet terminus 20 and upstream from the sample outlet terminus 22. Located at the sample inlet terminus 20 is a cylindrical conduit 26 that extends through surface 16. Five additional cylindrical conduits, 28, 30, 32, 34, 36 also extend through substrate 12 and, in combination with conduit 26, represent the vertices of an equilateral hexagon.

The microfluidic device 10 also includes a cover plate 40 that is complimentarily shaped with respect to the substrate 12 and has first and second substantially planar opposing surfaces indicated at 42 and 44, respectively. The contact surface 42 of the cover plate 40 is capable of interfacing closely with the contact surface 14 of the substrate 12 to achieve fluid-tight contact between the surfaces. The cover plate 40 is substantially immobilized over the substrate contact surface 14, and the cover plate contact surface 42 in combination with the sample micro channel 18 defines a sample conduit 25 for conveying the sample. Similarly, the cover plate 40, and in combination with the make-up fluid channel 24, defines a make-up fluid conduit 27 for conveying make-up fluid from a make-up fluid source (not shown) to the fluid sample conduit. Because the contact surfaces of the cover plate and the substrate are in fluid-tight contact, the sample conduit and the make-up fluid conduit are fluid tight as well. The cover plate 40 can be formed from any suitable material for forming the substrate 12 as described below. Further, the cover plate 40 can be aligned over the substrate contact surface 14 by any of a number of micro alignment means. To ensure that the sample conduit is fluid-tight, pressure-sealing techniques may be employed, e.g., by using external means (such as clips, tension springs or an associated clamp), by using internal means (such as male and female couplings) or by using of chemical means (e.g., adhesive or welding) to urge the pieces together. However, as with all embodiments described herein the pressure sealing techniques may allow the contacts surfaces to remain in fluid-tight contact under an internal microfluidic device fluid pressure of up to about 100 megapascals, typically about 0.5 to 40 megapascals.

As shown in FIG. 1A, the cover plate 40 and the substrate 12 may be discrete components. In such a case, micro alignment means described herein or known to one of ordinary skill in the art may be employed to align the cover plate with the substrate. In some instances, however, the substrate and the cover plate may be formed in a single, solid flexible piece. Microfluidic devices having a single-piece substrate and cover plate configuration have been described, e.g., in U.S. Pat. Nos. 5,658,413 and 5,882,571, each to Kaltenbach et al.

The cover plate 40 may include a variety of features. As shown, a sample inlet port 46 is provided as a cylindrical conduit extending through the cover plate in a direction orthogonal to the cover plate contact surface 42 to provide communication between surfaces 42 and 44. Although axial symmetry and orthogonality are preferred, the sample inlet port 46 does not have to axially symmetrical or extend in an orthogonal direction with respect to the cover plate contact surface. The inlet port 46 can be arranged to communicate with the conduit 32 of the substrate 12. As shown, the inlet port 46 has a substantially constant cross-sectional area along its length. The sample inlet port 46 enables passage of fluid from an external source (not shown) through conduit 32 to communicate with switching plate 60 as discussed below. The cross-sectional area of the inlet port should correspond to the cross-sectional area and shape of conduit 32. Similarly, two additional cylindrical conduits, i.e., waste port 48 and mobile phase inlet port 50 are provided fluid communication with conduit 30 and 36, respectively. Further, make-up fluid port 40 is also provided to allow make-up fluid from a make-up fluid source to be introduced into make-up fluid conduit 28.

A linear channel 52 having two termini, indicated at 54 and 56, is located in contact surface 42. The termini 54, 56 fluidly communicate with the conduits 34, 28, respectively. The termini 54 and 56 in combination with conduits 46, 48 and 50 represent five of six vertices of an equilateral hexagon. Accordingly, each of the conduits is located the same distance from the center point of the channel 52. As discussed above, the cover plate 40 is substantially immobilized over the substrate contact surface 14. As a result, substrate source 14 in combination with channel 52 forms a conduit 53, which serves as a sample-loading chamber, discussed below. Alternatively, the linear channel 52 may be provided on substrate surface 14. In such a case, termini 54 and 56 would coincide in location with conduits 34 and 28 respectively.

The sample conduit 25 is constructed for separation, and the device may therefore exhibit any micromachined structure appropriate for liquid chromatography. For example, U.S. Pat. No. 6,156,273 describes a micromachined liquid chromatography structure with a mass spectrometer interface. In addition, the conduit may contain any of a number of known liquid chromatographic packing materials may be included in the sample conduit. Such packing materials typically exhibit a surface area of about 100 to about 500 $m^2/g$. The conduit 25, for example, may be adapted to separate fluid sample components according to molecular weight, polarity, hydrophobicity or other properties through techniques known to one of ordinary skill in the art, e.g., through proper selection of packing materials. In addition or in the alternative, the interior surface of the conduit may be chemically, mechanically or otherwise modified using techniques known in the art to carry out separation of the components of a fluid sample according to a selected property. For example, U.S. Ser. No. 09/233,694 ("A Method for Producing High-Surface Area Texturing of a Substrate, Substrates Prepared Thereby and Masks for Use Therein"), inventors Brennen and Swedberg, filed on Jan. 19, 1999, describes a laser ablated high surface area micro channel; U.S. Pat. No. 5,770,029 describes a electrophoretic microfluidic device that allows for integrated sample enrichment means using a high surface area structure, U.S. Pat. No. 5,334,310 describes a micro channel having in-situ generated polymer therein. Thus, the interior surface of the conduit may exhibit surface characteristics such absorption properties and surface area similar to that associated with packing materials. In any case, typical samples may contain biomolecules such as nucleotide and/or peptide moieties.

A switching plate 60 is provided as a means for delivering a predetermined volume of fluid sample. This switching plate 60 is similar to that described in U.S. Ser. No. 09/908292 ("Flow-Switching Microfluidic device") inventors Killeen and Yin.

As shown in FIG. 1A, the switching plate 60 has a substantially planar and circular contact surface 62 and an opposing contact surface 64. As shown, the surfaces 62 and 64 are generally congruent. Three curved fluid-transporting channels, indicated at 66, 68 and 70, are each located on contact surface 62. The fluid-transporting features lie along a circle having a diameter equal to the length of channel 52. Each fluid-transporting channel has two termini: termini 72 and 74 are associated with feature 66, termini 76 and 78 are associated with feature 68, and termini 80 and 82 are associated with feature 70. An optional handle 84 that provides for each in manipulation of the switching plate 60 extends outwardly from the center of the channels.

The switching plate contact surface 62 may be placed in slidable and fluid-tight contact with substrate surface 16. As a result, the fluid-transporting channels, 66, 68 and 70, in combination with substrate surface 16, form three curved conduits, 67, 69, 71, respectively.

Figure 1B:
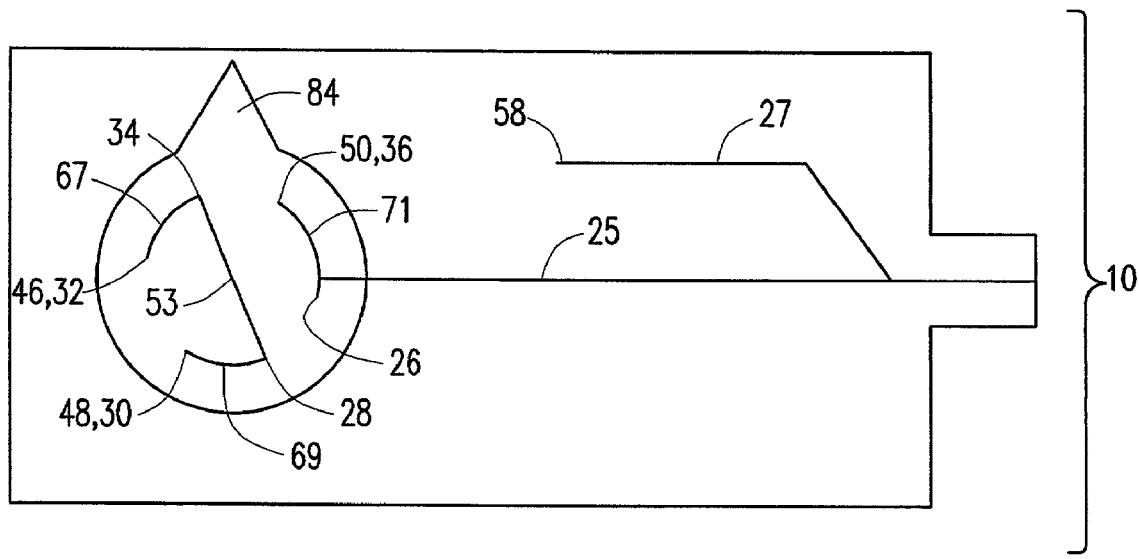
Figure 1C:
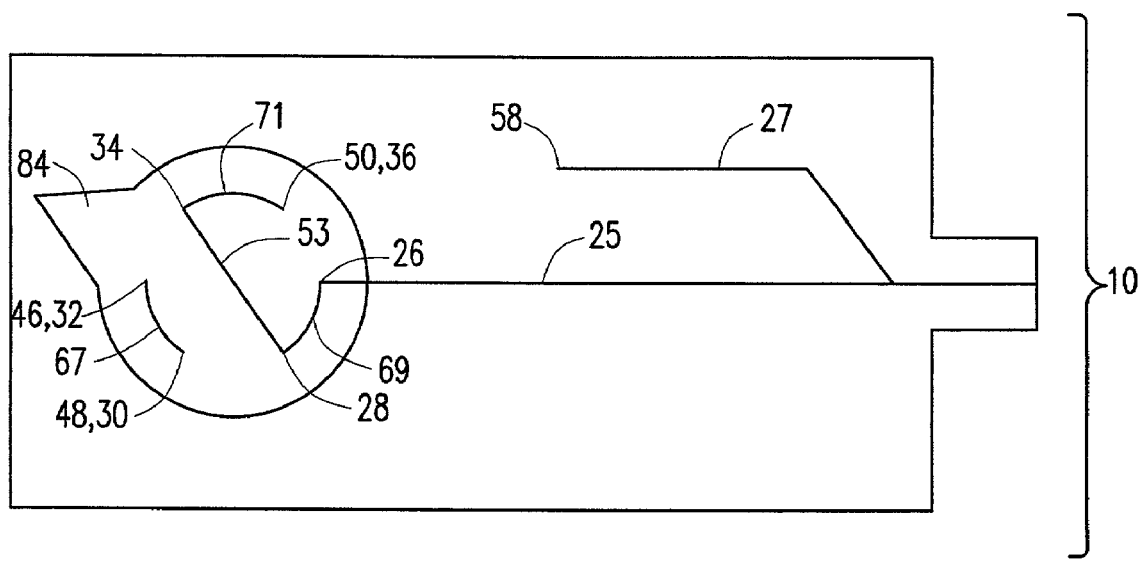

Depending on the relative orientation of the switching plate and the substrate, at least two possible flow paths configurations can be created. As shown in FIG. 1B, the first flow path configuration allows a fluid originating from sample inlet port 46 to travel, in order, through conduit 32, conduit 67, conduit 34, conduit 53, conduit 28, conduit 69, conduit 30 and waste port 48. The first flow path configuration also allows a fluid originating from mobile phase inlet port 50 to travel, in order, through conduit 36, conduit 71, conduit 26 and conduit 25. By rotating the switching plate 60 60° about its center, a second flow path configuration results, as shown in FIG. 1C. The second flow path configuration allows fluid originating from sample inlet port 46 to travel, in order, through conduit 32, conduit 67, conduit 30, and waste port 48. In addition, the second flow path configuration allows fluid originating from conduit 50 to travel, in order, through conduit 36, conduit 70, conduit 34, conduit 53, conduit 28, conduit 69, conduit 26 and sample conduit 25.

In use, the microfluidic device operates in a manner similar to a simple capillary liquid chromatographic apparatus. The switching plate 60 of the microfluidic device is arranged to result in a first flow path configuration as discussed above. A pump generates a high-pressure gradient to deliver a mobile phase through mobile phase inlet port 50, conduit 36, conduit 71, conduit 26 and conduit 25. In order to control the internal pressure of the microfluidic device and the flow rate of the mobile phase, a splitter, integrate or otherwise, may be employed to divert a portion of the mobile phase before entry into the conduit 50. In addition, fluid sample is injected into sample inlet port 46 from a sample source. As a result, the fluid sample forms a contiguous body of fluid that flows, through sample inlet port 46, conduit 32, conduit 67, conduit 34, conduit 53, conduit 28, conduit 69, conduit 30 and waste port 48. The sample emerging from conduit 66 may be collected and recycled.

By forming a second flow path configuration as discussed above, the conduit 53 is now positioned in the flow path of the mobile phase entering the microfluidic device through conduit 50. That is, the mobile phase is now pumped through a flow path that travels, in order, through conduit 50, conduit 36, conduit 70, conduit 34, conduit 53, conduit 28, conduit 69, conduit 26 and sample conduit 25. Thus, fluid sample remaining within conduit 53 is also forced through separation conduit 25. It should be evident, then, that by rotating the substrate of the switching assembly, a predetermined volume of fluid sample defined by conduit 53 is controllably introduced from a sample source into the separation conduit 25 of microfluidic device 10. The sample plug is then separated into sample components according to a component property and emerges from sample outlet port. The outlet may be interfaced with a collector, such as a sample vial, plate or capillary. The collector may serve as a storage device or represent an intermediary to another device that uses and/or analyzes collected fraction. Alternatively, an analytical device may be directly interfaced with the outlet port for fraction analysis.

It should be noted that an analyzer may be interfaced with any portion of the flow path of the inventive microfluidic device including the inlet port. The analyzer may be, for example, a mass spectrometer, in which case the outlet port may be located within or adapted to deliver fluid sample to an ionization chamber. See U.S. Ser. No. 09/711,804 ("A Microfluidic device Having an Integrated Protruding Electrospray Emitter and a Method for Producing the Microfluidic device"), inventors Brennan, Yin and Killeen, filed Nov. 13, 2000. In addition, mass spectrometry technologies are well known in the art and may involve, for example, laser desorption and ionization technologies, whose use in conjunction with microfluidic devices are described in U.S. Pat. Nos. 5,705,813 and 5,716,825. In the alternative or in addition, the analyzer may be a source of electromagnetic radiation configured to generate electromagnetic radiation of a predetermined wavelength. Depending on the intrinsic properties of the fluid sample and/or any molecular labels used, the radiation may be ultraviolet, visible or infrared radiation.

It should be noted that other aspects of known separation technology may be incorporated into the practice of the present invention. For example, when ordinary liquid chromatography packing material is slurry packed within the separation conduit, a frit structure, micromachined or otherwise, may be included near or at the sample outlet port. The frit structure serves to ensure that the packing material is not displaced from within the sample conduit when a fluid sample and/or a mobile phase are conveyed through the conduit. In addition, it is preferred that the cross-sectional area of the separation conduit is reduced downstream from the frit structure, particularly if the sample outlet port is a part of an electrospray tip as described, for example, in U.S. Ser. No. 09/711,804 ("A Microfluidic device Having an Integrated Protruding Electrospray Emitter and a Method for Producing the Microfluidic device"), inventors Brennen, Yin and Killeen, filed on Nov. 13, 2000. In addition, multiple liquid chromatography columns can be included in a single microfluidic device. Such microfluidic devices may involve parallel sample introduction from one or a plurality of sample sources followed by serial separation or parallel sample separation. Thus, in another embodiment, the invention relates to a microfluidic device for separating the components of a fluid sample having at least one additional micro channel. In this embodiment, a first and a second micro channel are formed in the first surface and the cover plate in combination with the first and second micro channels defining a first and a second conduit, respectively. The sample inlet port is in fluid communication with a valve and the valve is constructed for providing selective fluid communication between the inlet port and either one of the conduits. As a result, a fluid sample introduced from a sample source can be conveyed in a defined sample flow path that travels, in order, through the sample inlet port, the selected conduit, and a sample outlet port associated with the selected conduit. At least one of the conduits is constructed for separating the components of the fluid sample according to a component property. Preferably, each of the conduits is constructed for separating the components of the fluid sample according to a different component property.

Figure 2A:
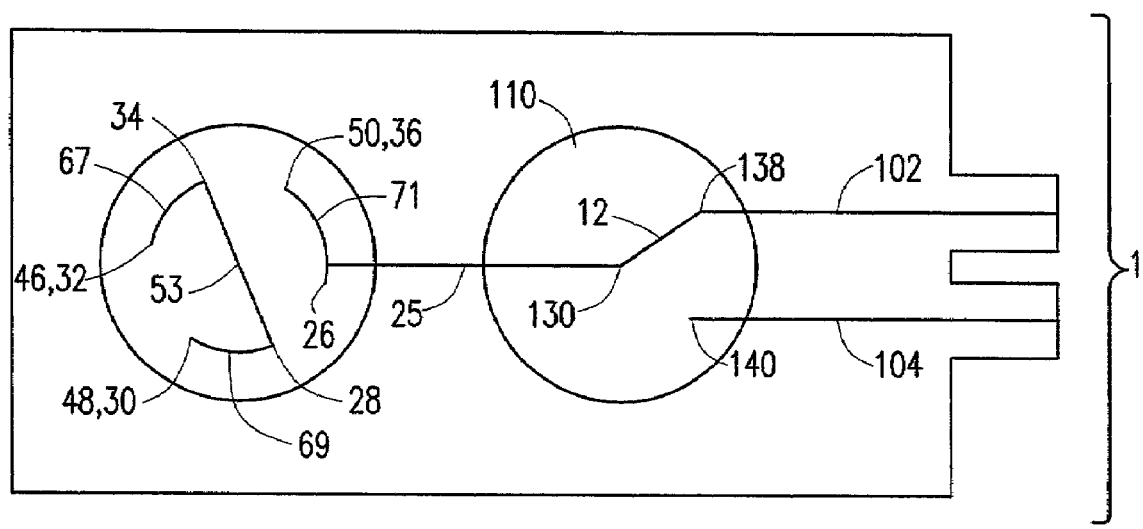
FIGS. 2A and 2B, collectively referred to as FIG. 2, illustrate another embodiment of the inventive microfluidic device that employs two parallel conduits.

This embodiment is illustrated in FIG. 2. This embodiment is similar to that illustrated in FIG. 1 in that the microfluidic device 10 employs a switching structure that uses rotational and sliding motion to controllably introduce a predetermined volume of fluid sample to a separation conduit. However, in this embodiment, the microfluidic device includes additional features as well. As illustrated in FIG. 2, additional conduits indicated at 102 and 104 are provided downstream from conduit 25. A valve 110 is interposed between conduit 25 and additional conduits 102 and 104. The valve 110 is constructed for allowing a fluid sample to flow from conduit 25 to no more than one of conduits 102 and 104 at a time.

Figure 2B:
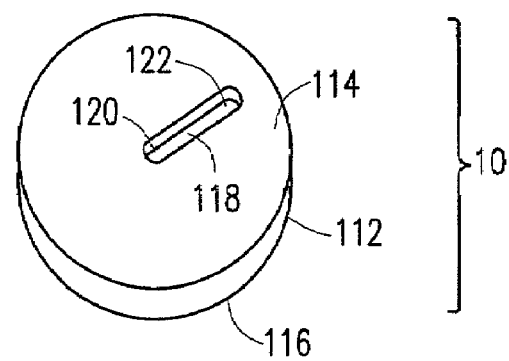

A variety of valve types known in the art can be employed to selectively provide fluid communication between conduit 25 and conduits 102 and 104. Known valve types include, but are not limited to, ball valves, solenoid valves and gate valves. It is preferred that the valve is constructed as a integrated portion of the inventive microfluidic device. Thus, as illustrated in FIG. 2B, the valve 110 may include a cylindrical valve plate 112 having a contact surface 114 and an exterior surface 116. In such a case, the contact surface 112 and the exterior surface 114 of the valve plate are typically substantially planar opposing. The valve plate 112 has a fluid-transporting feature in the form a valve micro channel 118 in the first planar surface 114. The valve micro channel 118 has an inlet terminus 120 at one end and an outlet terminus 122 at another end. The inlet terminus 122 is closer to the edge of the valve plate 112. When the contact surface of the valve plate is placed in fluid-tight contact with an exterior surface of either the substrate 12 of the cover plate 40, the exterior surface in combination with the micro channel forms a fluid-tight valve conduit 119.

In this configuration, either the cover plate or the substrate includes a valve inlet port 130 and valve outlet ports 138 and 140 as cylindrical conduits extending therethrough. The valve inlet port 130 is positioned to allow fluid to flow from the downstream terminus of the conduit 25 and the inlet terminus 120 of the valve micro channel. Although axial symmetry and orthogonality are preferred, the valve inlet port does not have to be axially symmetrical or extend in an orthogonal direction with respect to the substrate contact surface. The inlet port 130 may have a substantially constant cross-sectional area along its length, and the cross-sectional area of the inlet port should correspond to the width of the valve micro channel 118 and to the shape of the micro channel at the inlet terminus 120.

The valve outlet ports are located the same distance from the valve outlet port, the distance being the length of valve micro channel. The valve outlet ports 138 and 140 are positioned to allow fluid to flow to conduits 102 and 104, respectively. By rotating valve plate 112, selective fluid communication can be provided between inlet port 130 and conduits 102 and 104. As discussed above, each conduit may be provided with different packing materials selected according to the fluid sample and the desired separation technique.

Instead of carrying out parallel separation, multiple liquid chromatography columns can be included in a single microfluidic device to carry out multidimensional separations, i.e., separation in series. Thus, in another embodiment, a microfluidic device is provided that includes a first integrated introducing means for controllably introducing the fluid sample from a sample source through a sample inlet port in fluid communication with the first conduit, and a second integrated introducing means for controllably introducing fluid sample from the first conduit through the second conduit and an outlet port. At least one of the conduits is constructed for separating the fluid according to a component property. In this embodiment, then, a flow path joins at least one additional conduit in series with a separation conduit and thus provides for multidimensional separation providing that at least one additional conduit is adapted for separation.

Figure 3:
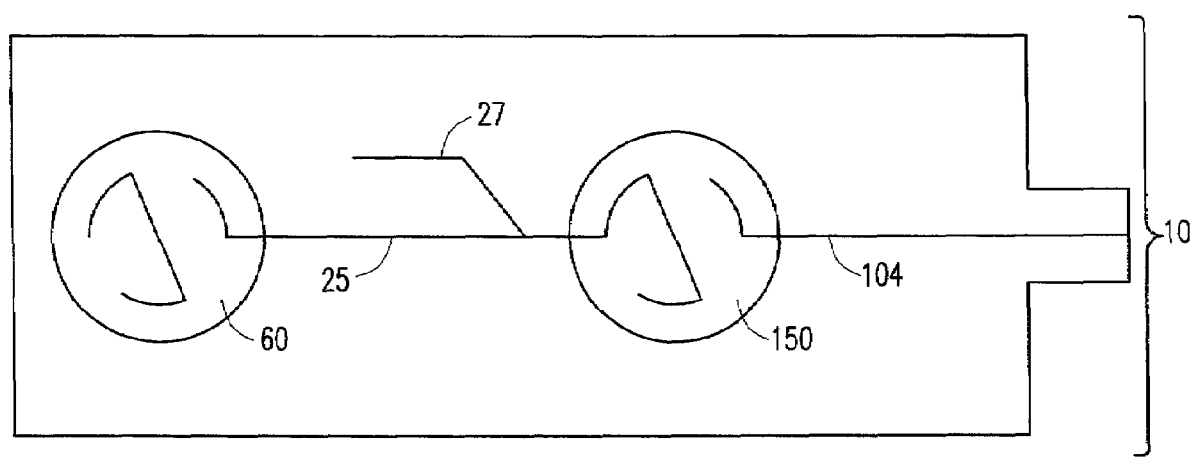
FIG. 3 schematically illustrates a further embodiment of the inventive microfluidic device that may be used to carry out separation in series.

This embodiment is illustrated in FIG. 3. Microfluidic device 10 includes an introducing means in the form of a switching plate 60 as illustrated in FIG. 1 that employs rotational motion to controllably introduce a predetermined volume of fluid sample into a separation conduit. The microfluidic device includes a second integrated introducing means 150 for controllably introducing means 150 may be of the same or different construction as the switching assembly discussed above. In addition, as illustrated in FIG. 3, an additional conduit 104 is provided downstream from the inlet port. This additional conduit may be employed in a second dimensional separation. For example, the first conduit may provide a first dimension of separation for nucleotide or peptide moieties through size exclusion chromatography, ion chromatography, capillary electrophoresis, isoelectric focusing, or eletrophoretic focusing via field gradient. Then, fractions from the first dimension separation can be directed into an optional reaction chamber within the integrated introducing means filled with a reaction catalyst, e.g., in the form of catalyst-modified beads. In this case, proteins are separated in the first dimension and they are then subjected to digestion in the reaction chamber, followed by second dimension separation in the secondary conduit.

In addition to the switching assembly, other integrated introducing means may also be employed. Typically, an integrated introducing means comprises a loading chamber sized to hold a predetermined volume of fluid sample. By constructing the loading chambers to allow for switchable fluid communication with either the sample source or the mobile phase source, a predetermined volume of fluid sample may be loaded into the chamber or removed therefrom. That is, the loading chamber assists in the accurate and precise handling of a predetermined volume of fluid sample. In addition, the loading chamber ensures that the fluid sample is introduced as a contiguous body, so as to enhance separation resolution. To ensure convenience and ease of switching, it is preferred that fluid communication is achieved through a sliding motion. Similarly, the integrated introducing means may comprise a valve constructed for actuation through a sliding motion. Rotational and linear sliding motion may be used in either case. In addition, mechanisms relating to on-device features that can be used to uptake sample from a sample source such as vials and titer plates may be employed as well in interfacing relation to the introduction means. See U.S. Ser. No. 09/570,948, inventors Zimmerman and Ple, filed on May 15, 2000.

Any of the above-described microfluidic devices may separate the fluid sample according to one or more sample properties. For example, a component property may be molecular weight, polarity, hydrophobicity or charge. To enhance separation performance, the microfluidic device may include a mobile phase source, in fluid communication with the integrated introducing means and/or employs as a make-up fluid source. When the mobile phase source is employed in conjunction with the integrated introducing means, the integrated introducing means may provide fluid communication between the mobile phase source and the separation conduit through a bypass. This is particularly useful when a loading chamber is employed, insofar as loading of the chamber is made possible by providing the loading chamber in fluid communication with a sample source.

The microfluidic devices may employ operation principles similar to those of ordinary liquid chromatography devices. Thus, there are instances in which ordinary liquid chromatography technology may be incorporated in the practice of the invention. For example, a fluid flow rate regulator for regulating flow rate may be employed to ensure that a mobile phase is delivered to the separation conduit at an appropriate rate and pressure. Such flow rate regulators may be interposed in the flow path between the mobile phase source and the integrated introducing means. The flow rate regulator may also include a flow splitter. Additionally, a flow sensor for determining and optionally controlling the rate of fluid flow into the sample inlet source may be provided. Similarly, as it is known in the art that more than one solvent may be employed to carry out ordinary liquid chromatography processes, the microfluidic device may include a mobile phase source comprises a mixer for mixing solvents. Further, temperature control means may provide reproducible separation performance.

In another embodiment of the invention, a method is provided for separating the components of a fluid sample. In order to carry out the method, a microfluidic device is provided as above. The method involves controllably introducing a predetermined volume of a fluid sample from a sample source into a sample inlet port, conveying the fluid sample through the conduit, thereby separating the components of the fluid sample; and analyzing the sample collected at the sample outlet port. An analyzer as described above is provided for carrying out the last step of the method.

From the above description of the various embodiments of the invention, it is evident that the integrated introducing means may introduce a predetermined volume of fluid sample appropriate to the desired separation process and the dimensions of the microfluidic device. Typically, the predetermined volume is less than about 5 microliters. Preferably, the predetermined volume is about 0.01 to about 0.1 microliters. It should also be evidence that the switching assembly provides for greater control in carrying out chemical or biochemical reactions and processes for sample preparation and analysis.

Thus, variations of the present invention will be apparent to those of ordinary skill in the art. For example, additional features may be included to carry out known reactions and processes, for example, reactions and processes associated with sample preparation, synthesis and analysis. Such features may be formed from conduits and channels that provide for fluid flow in a parallel or nonparallel direction with respect to the contact surfaces. In addition, the integrated introducing means may be used to carry out digestion of the fluid sample before the sample is introduced into the separation conduit. That is, the conduit of the integrated introducing means may be filled with a moiety that digests the fluid sample. When the fluid sample contains peptide moieties, commonly used proteolytic enzyme such as trypsin and pepsin may be employed. Similarly, when the fluid sample contains nucleotide moieties, nuclease enzymes capable of nucleotide digestion, e.g., endonucleases and exonucleases, may be used. Moreover, additional substrates of a variety of shapes may be employed. Locking mechanisms may also be provided in order to a greater degree of control over the position of the contact surfaces of the switching assembly.

Figure 4:
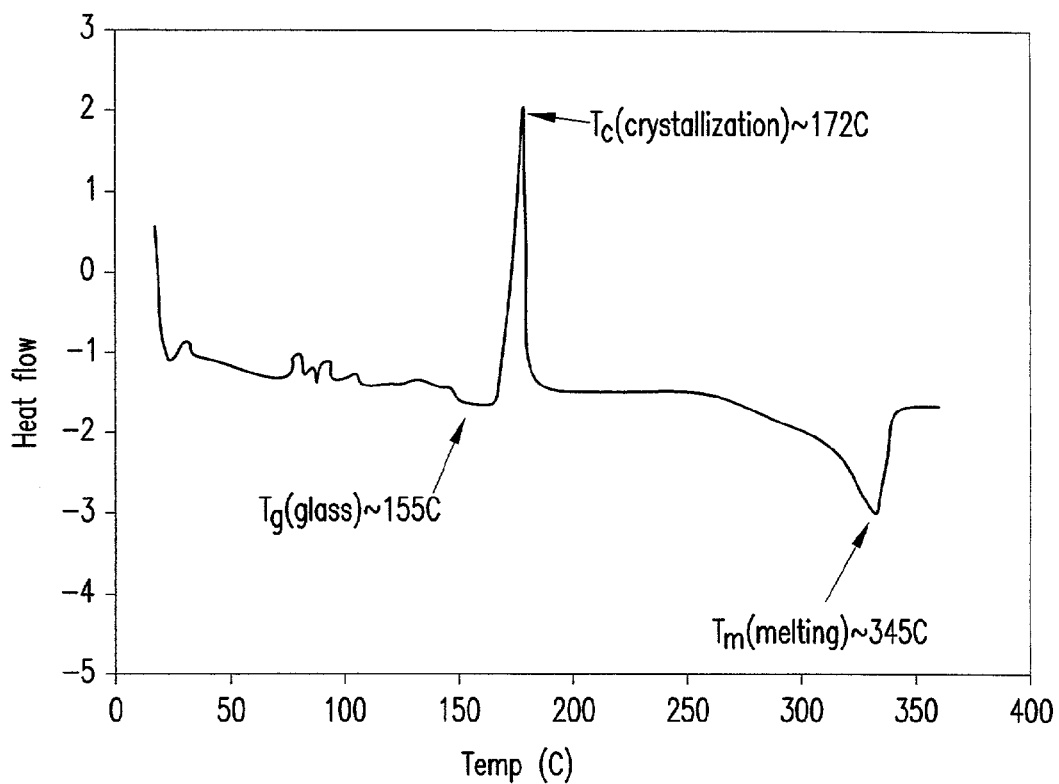
FIG. 4 is an exemplary representation of the first temperature scan PEEK that is primarily glassy.

In any of the above embodiments, at least one of the materials for forming the substrates and cover plates is a polyaryl-ether-ketone (PAEK) material, such as polyether-ether-ketone (PEEK), polyether-ketone-ether-ketone-ketone (PEKEKK) and polyether-ketone-ketone (PEKK). PAEK materials are semicrystalline polymers that have several desirable properties for microfluidic applications. Such properties include high mechanical modulus, toughness, low thermal distortion and high chemical resistance. In addition, PAEK materials also have high melting temperatures as compared to their glass transition temperatures, and thus, PAEK materials have large processing windows between the crystallization from the glassy state $(T_c)$ and melting $(T_m)$. For example, as shown in FIG. 4, PEEK has a glass transition temperature $(T_g)$ of around 155° C. (+/−5 degrees) and a melting point temperature $(T_m)$ that varies depending on the temperature of crystallization $(T_c)$. As an example, when the crystallization temperature $(T_c)$ of PEEK from the glass state is around 172° C. (+/−5 degrees), the melting point temperature $(T_m)$ is around 345° C. (+/−5 degrees).

Molten PEEK can be "quenched" into a non-crystalline (or low crystallinity) material by rapidly cooling the melt below the glass transition temperature $(T_g)$. A sheet of quenched PEEK is an amorphous, non-crystalline glass that has a translucent appearance. It should be noted that since rapid cooling is required, glassy PEEK is preferably processed in film form, on the order of 100 microns thick. Thin films of amorphous PEEK are available from various manufacturers and distributors, such as Victrex and Westlake Plastics.

The processing window created by the temperature difference that exists between the glass transition temperature $(T_g)$ (around 155° C.) and melting point $(T_m)$ (345° C.) allows for embossing of PEEK. The large processing window results from the fact that PEEK crystallizes relatively slowly due to the fact that PEEK has stiff chains (unlike other thermoplastics, such as polyethylene or polypropylene, that have flexible chains that fold quickly into crystals). Since the sheet of quenched PEEK becomes ductile above 155° C., the PEEK sheet is capable of being embossed above 155° C., but below 345° C. In addition, once the PEEK sheet reaches a temperature at or above a crystallization temperature corresponding to relatively rapid crystallization from the glass state, the PEEK sheet becomes rigid as it crystallizes, which enables the PEEK sheet to maintain the shape of the embossed pattern at this temperature.

Figure 5:
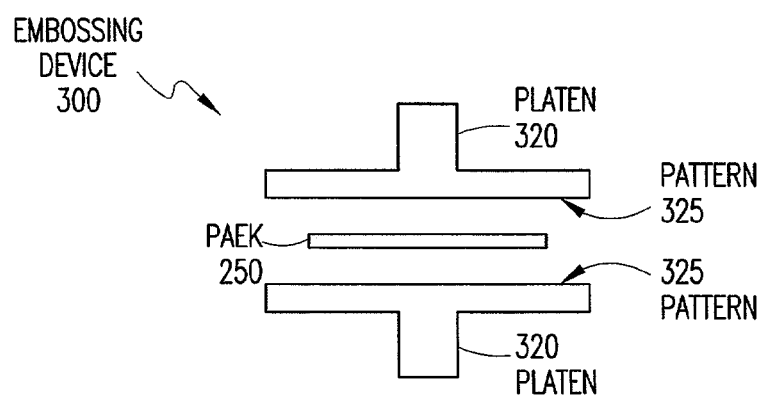
FIG. 5 is a side view of an exemplary embossing device for embossing a thin film of PAEK.

Referring now to FIG. 5, which illustrates a side view of exemplary embossing device 300, a quenched sheet of PAEK 250 can be heated up to the glass transition temperature by either placing the PAEK sheet 250 in an oven (not shown) or heating the PAEK sheet 250 using heating elements built inside platens pressed on the PAEK, the latter being illustrated. Once the PAEK sheet 250 reaches the glass transition temperature, the PAEK sheet 250 can be embossed with patterns by applying pressure to the PAEK sheet between platens 320 containing negative patterns 325 of the desired features. The platens 320 can be made of any hard material, such as metal or ceramic. While the platens 320 are being pressed onto the PAEK sheet 250, the temperature of the PAEK sheet 250 is brought up further to at or above the crystallization temperature. After the features are embossed onto the PAEK sheet 250, the platens 320 can be removed from the PAEK sheet 250. It should be noted that the platens 320 can be pressed down onto the PAEK sheet 250 when the PAEK sheet 250 is at any temperature between the glass transition temperature and the crystallization temperature.

Advantageously, the platens 320 can be maintained at a narrow temperature range without the need to cycle the platens 320 through the melting point temperature of PAEK. The pressure cycle, which includes the duration of time necessary to bring the temperature of the PAEK sheet 250 up to the glass transition temperature, can be readily ascertained using known methods in the art. Therefore, once the platens 320 are pressed onto the PAEK sheet 250, a timer (not shown) can be set, and once the timer expires, the platens 320 can be removed from the PAEK sheet 250. The embossed PEEK sheet 250, which now has a shiny opaque appearance, can be removed from the platens 320 and another cold sheet of quenched PEEK 250 that has a translucent appearance can be placed between the platens 320.

In order to fabricate a microfluidic device using PAEK substrate material 250, at least two separate substrates, at least one of which is a PAEK substrate 250, are bonded together to form channels where gases or liquids may move to accomplish the various applications the microfluidic device is designed for. For example, as shown in FIGS. 3A and 3B, the microfluidic device 400 can include at least one patterned PAEK substrate 250 having an internal cavity 260 forming at least a part of a lumen or channel. However, it should be understood that the at least one PAEK substrate 250 does not have to be patterned. Instead, the PAEK substrate 250 could have a flat surface.

Figure 6A:
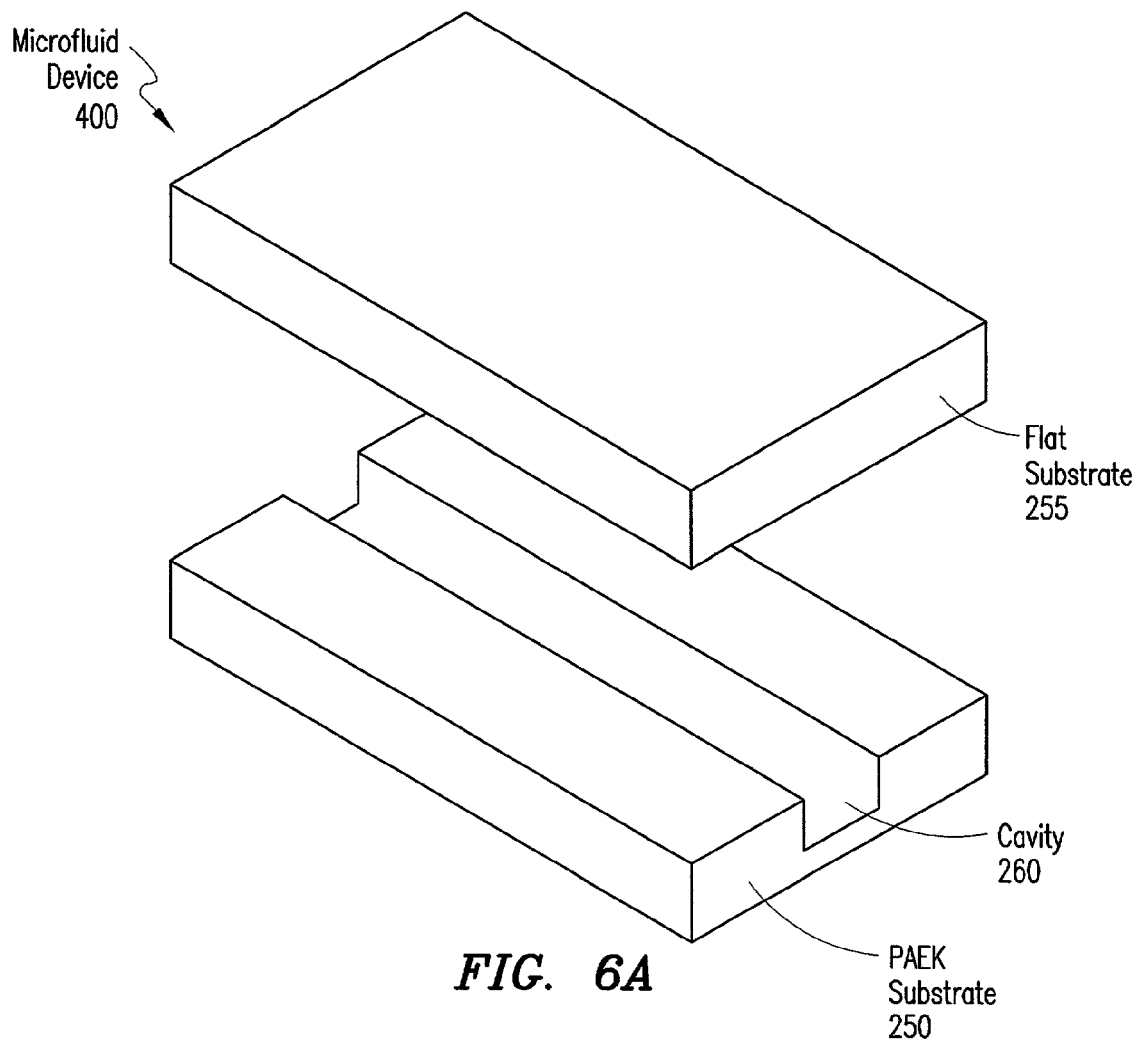
FIGS. 6A and 6B are illustrative views of patterned PAEK substrates.
Figure 6B:
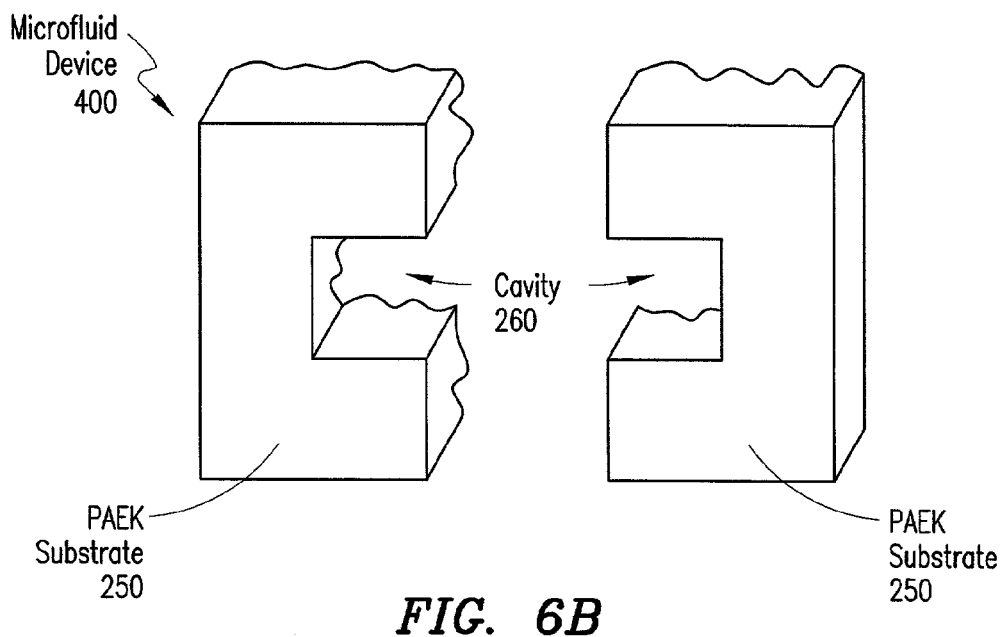

FIG. 6A illustrates one patterned PAEK substrate 250 having the internal cavity 260 and another flat substrate 255 that can be bonded with the patterned PAEK substrate 250 to form a microfluidic device 400. The flat substrate 255 can be formed of any solvent-resistant material, including, but not limited to, PAEK or glass. FIG. 6B illustrates two patterned PAEK substrates 250, each having a respective internal cavity 260. When bonded, the internal cavities 260 of the two patterned PAEK substrates 250 combine to form a lumen or channel of the microfluidic device 400. It should be understood that the patterned PAEK substrate 250 can be formed using any fabrication technique, including embossing, as described above, laser ablation, injection molding, etc.

It should be understood that the microfluidic device 400 can include multiple channels, and each channel can include one or more pillars to form the molecular separation media depending upon the application of the microfluidic device. It should also be understood that the microfluidic device 400 can be filled with chromatographic media prior to bonding or, alternatively, the chromatographic media can be injected into the microfluidic device 400 via an injection interface (as described above).

Figure 7A:
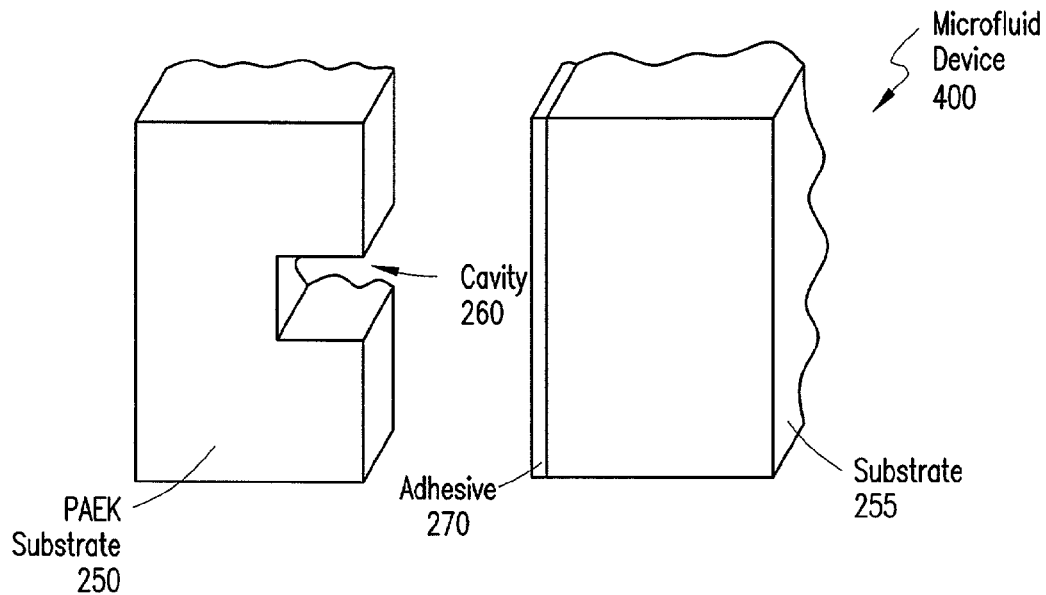
FIGS. 7A and 7B are illustrative views of patterned PAEK substrates with polyimide-based adhesive material thereon.
Figure 7B:
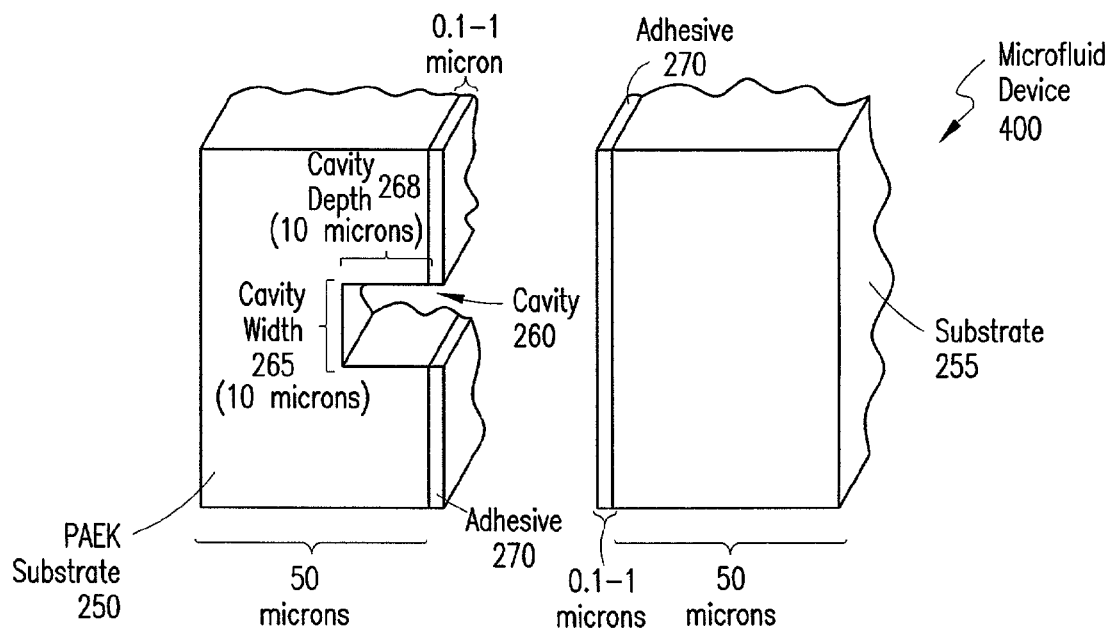

Referring now to FIGS. 7A and 7B, to bond the patterned PAEK substrate 250 to another substrate 255, a layer of a solvent-resistant adhesive 270, such as a polyimide-based adhesive, is applied to the surface of at least one substrate. For example, the polyimide-based adhesive 270 can include one of the thermoplastic imide-based materials developed initially by the NASA-Langley Research Center and commercially marketed by IMITEC, Inc. of Schenectady, N.Y. Desirable properties of the thermoplastic imide-based materials include a melting point well-below that of the laminate layers (PAEK in this instance), the capability to harden and the ability to be applied as a bond between respective layers. Other commercially available thermoplastic polyimides 270 that can be used as the polyimide-based adhesive 270 are discussed by D. J. Coulman et al. in U.S. Pat. No. 6,179,413, which is hereby incorporated by reference. As discussed in Coulman et al., manufacturers regard the structures of such thermoplastic polyimides proprietary. A general reference describing the structures and properties of thermoplastic polyimide materials can be found in S. Tamai et al., "Melt-processible polyimides and their chemical structures," *Polymer*, Vol. 37, pp. 3683-3692 (1996), which is hereby incorporated by reference.

For example, in one embodiment, the polyimide-based adhesive 270 contains a solution of approximately 10% of solid polyimide resin in N-methyl pyrrolidone (NMP). In other embodiments, instead of using a thermoplastic polyimide resin, the corresponding polyamic precursor polymers, mixtures of imidized polymers and polyamic acids and partially imidized polyamic acids can be used as the polyimide-based adhesive 270. The process of imidization during staking under pressure, vacuum and heat promotes (in some cases) better adhesion, especially when the solution-formulated resin is coated to only one side of the surfaces that are brought together for bonding. However, it should be understood that other solvent-resistant adhesives can be used instead of the polyimide-based adhesive discussed herein by way of example, and not limitation.

FIG. 7A illustrates the coating of one surface of only one substrate (here substrate 255, although it should be understood that either substrate 250 or 255 can be coated with the adhesive 270) with the solvent-resistant adhesive 270, while FIG. 7B illustrates the coating of the surface of both substrates 250 and 255 with the solvent-resistant adhesive 270. Applying the adhesive 270 to the surface of only one substrate 250 or 255 allows for the removal of charring material resulting from machining (e.g., laser ablation) from the surface of the substrate void of adhesive material 250 or 255. Additionally, if the intended application of the microfluidic device 400 requires a special chemical treatment (e.g., chemical modification, patterning or other thin film deposition) of the surface of the channel or outside the channel, the chemical treatment can be performed on the substrate 250 or 255 without the adhesive layer 270. It should be understood that the flat substrate 255 shown in FIGS. 7A and 7B can be formed of any solvent-resistant material, including, but not limited to, amorphous PAEK, crystalline PAEK, glass or polyimide.

In certain embodiments, the solvent-resistant adhesive layer 270 is thin as compared to the thickness of the substrate 250 or 255. For example, as shown in FIG. 7B, the patterned PAEK substrate 250 has a thickness of 50 microns, the cavity width 265 is 10 microns thick, the cavity depth 268 is 10 microns thick and the solvent-resistant adhesive layer 270 is 0.1-1 microns thick. The use of a thin layer of adhesive minimizes issues associated with excess adhesive material extruded into the channels, as well as reduces the effect of adhesive swelling that can occur under the presence of certain solvents, and therefore, improves the performance of the microfluidic device 400.

Figure 8:
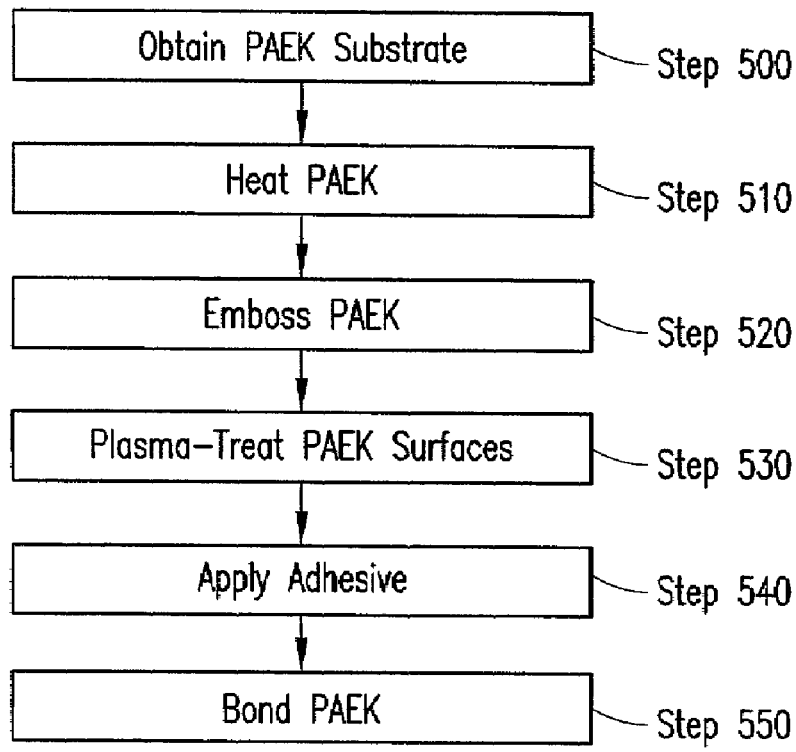
FIG. 8 is a flow chart illustrating the exemplary steps for fabricating a microfluidic device using PAEK.

Referring now to the steps shown in FIG. 8, an exemplary embodiment for fabricating a PAEK microfluidic device is illustrated. Each PAEK substrate of the microfluidic device is fabricated from amorphous (i.e., glassy) PAEK substrates (step 500). Thereafter, the glassy PAEK substrates are heated to the glass transition temperature, where the PAEK substrates become ductile (step 510) and begin to crystallize at the same time.

The ductile PAEK substrates are embossed with respective platens containing negative patterns of the desired features for each of the PAEK substrates by pressing the respective platens onto the PAEK substrates until the PAEK substrates achieve complete crystallization (step 520). Thereafter, the embossed PAEK substrates, which now contain the patterns for the microfluidic device, are prepared for bonding.

In order to effectively bond PEEK, an adhesion enhancement treatment is applied to the surfaces of the PAEK substrates (step 530). In one embodiment, a plasma treatment is used to prepare the surfaces of both PEEK substrates for bonding. The plasma treatment is described in more detail below in connection with FIG. 9. In another embodiment, a chemical sulfonation treatment of the type described in "POLY(ARYL ETHER KETONE) (Functionalization)" by Roovers and Wang in *Polymeric Materials Encyclopedia* (*PME*), edited by Joseph Salamone (CRC press 1996), which is hereby incorporated by reference.

To bond a stack of two or more plasma-treated substrates of PAEK, a solvent-resistant adhesive, such as a polyimide-based adhesive, is applied to all the surfaces facing each other or to just one of each of the surfaces facing each other (step 540). The adhesive can be applied using any deposition method, including, but not limited to, spin-casting, brushing, doctor-blade coating, spraying, screen-printing, jet-printing, dip-coating, Gravure coating and reverse roll coating. For example, in one embodiment, the amount of resin in a polyimide-based adhesive is diluted to approximately 10% solid polyamic acids in N-methyl pyrrolidone (NMP). Thereafter, the two PAEK substrates, at least one of which contains the adhesive, are brought together and held under a vacuum under pressure and heat to bond the two PAEK substrates together (step 550).

Figure 9:
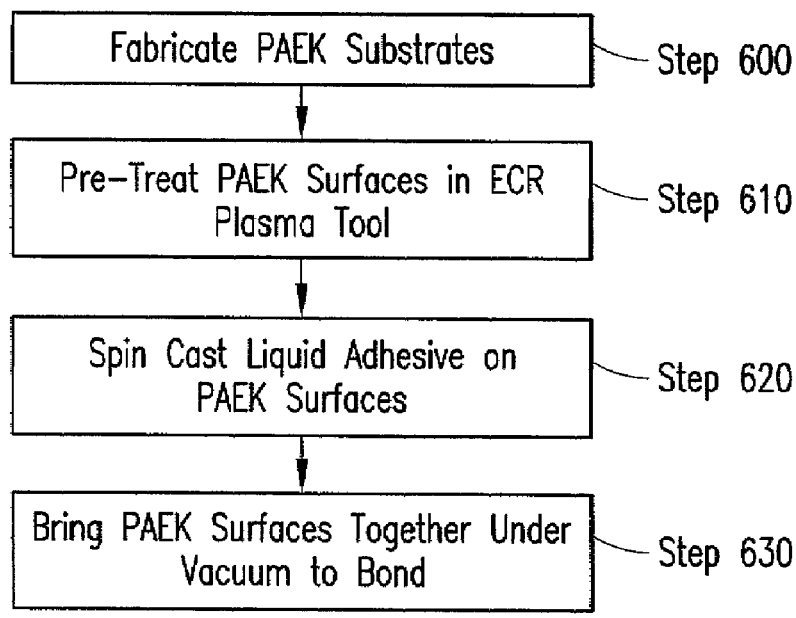
FIG. 9 is a flow chart illustrating the exemplary steps for bonding a microfluidic device using PAEK.

Referring now to FIG. 9, an exemplary process for bonding PAEK (as required for use in creating a microfluidic device or any other device using PAEK) using a plasma adhesion enhancement treatment is illustrated. However, it should be understood that some of the steps listed below can be removed, and other steps not listed can be added, depending upon the particular implementation. Once the PAEK substrates are fabricated (step 600), the surfaces of the PAEK substrates are pre-treated in an oxygen plasma with enough excitation to alter the PAEK surface sufficiently to bond to the solvent-resistant adhesive. (step 610). One example of a plasma treatment involves the use of a Plasma Tool with the following parameters:

| Plasma Tool Feature | Setting |
|---|---|
| $O_2$ Flow: | 30 sccm (Range: 10-100 sccm) |
| Ar Flow (optional): | 10 sccm |
| Source Power: | 900 Watts (Range: 500-900 Watts) |
| Bias Power: | 100 Watts (Range: 50-200 Watts) |
| Pressure: | 5 mTorr (Range: 0.1-10 mTorr) |
| Time: | 60 seconds (Range: 30-120 seconds) |

Thereafter, a thin film of a liquid solvent-resistant adhesive, such as a polyimide-based adhesive containing a solution of about 10% solid NMP, is spun cast on the plasma-treated surfaces at 2,000 rpm for 30 seconds (step 620). For example, in one embodiment, the adhesive can be produced from IMITEC's™ adhesive resin "051", which is a 40% solution of a thermoplastic polyimide resin in NMP. IMITEC's™ adhesive resin "051" is used primarily for bonding polyimide to various substrates, and to itself. However, by diluting IMITEC's™ adhesive resin "051" to contain approximately 10% solids in NMP, the adhesive can be used to bond PAEK, as described above. It should be noted that the processing temperature of the selected solvent-resistant adhesive is preferably substantially below the melting temperature of the PAEK material.

To dry the PAEK substrates coated with the adhesive resin, the PAEK substrates are rapidly annealed at about 90° C. in air for approximately 2-3 minutes. After drying, the thickness of the adhesive film on the PAEK surfaces is typically approximately 70 nm to 1 micron. Once dry, the temperature of the two PAEK substrates is increased to about 190° C. without pressure. Thereafter, the two PAEK substrates are brought together and held under a vacuum at approximately 190° C. and 250 psi for 10 minutes, and then at about 230° C. and 250 psi for another 30 minutes (step 530) to cure the adhesive resin. By curing under a vacuum, any volatile subproducts that might evolve during the curing of the resin can be removed. However, it should be understood that curing under a vacuum is not necessary in all applications. Upon cooling, the adhesive resin becomes imidized and resistant to solvents.

Figure 10:
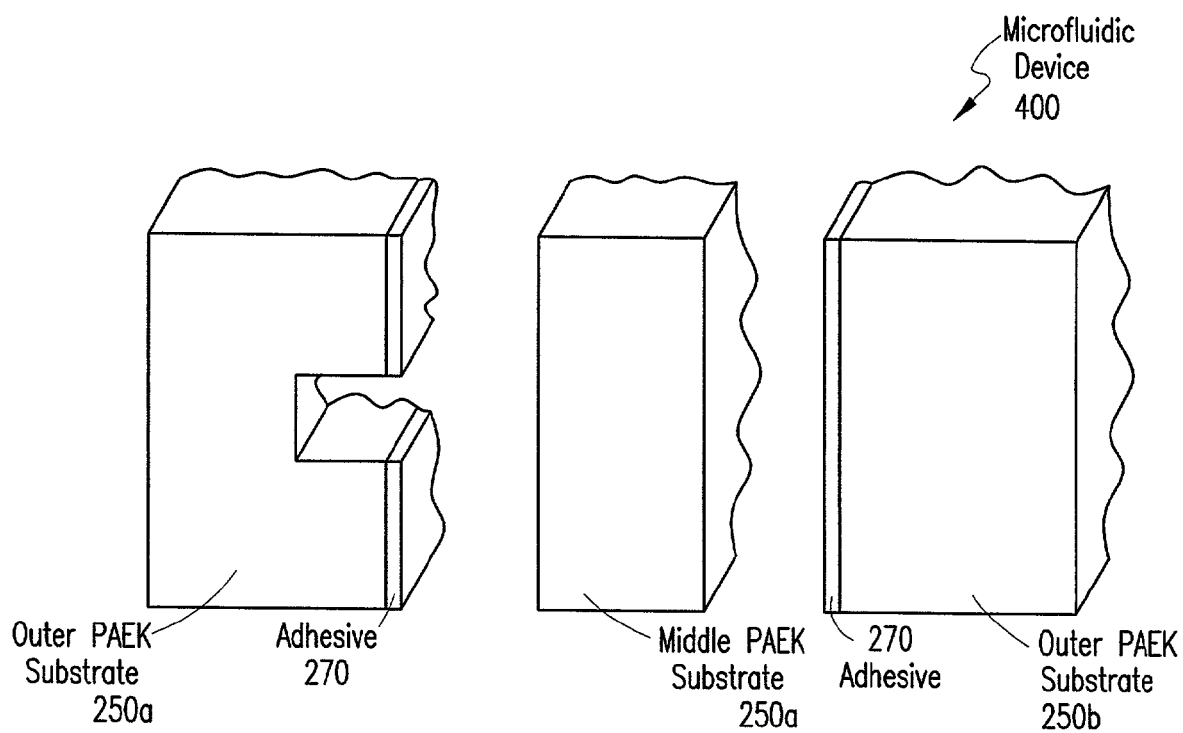
FIG. 10 is an illustrative view of a stack of three PAEK substrates, the outer two of which having polyimide-based adhesive material thereon.
Figure 11:
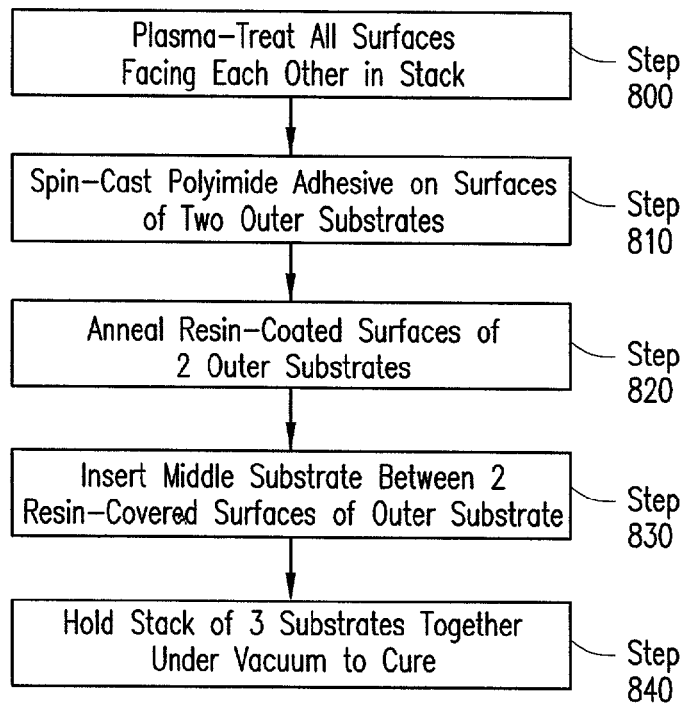
FIG. 11 is a flow chart illustrating the exemplary steps for bonding a stack of three PAEK substrates, as shown in FIG. 10.

Referring now to FIGS. 10 and 11, an actual and tested process for bonding a microfluidic device 400 is illustrated. FIG. 10 illustrates a stack of three crystalline PAEK substrates 250*a-c*, in which the two outer PAEK substrates 250*a* and 250*b* each have a respective surface coated with the solvent-resistant adhesive 270, while the two surfaces of the middle PAEK substrate 250*c* facing each of the adhesive-coated surfaces of the outer PAEK substrates 250*a* and 250*b* are not coated with the solvent-resistant adhesive 270.

Turning now to the steps illustrated in FIG. 11, to bond the three PAEK substrates to form a microfluidic device, the surfaces of the three PAEK substrates that faced each other were subjected to oxygen plasma (step 800) in a Technics model PE II A plasma system (Technics West). The conditions were: (1) $O_2$ pressure: 400 mTorr; (2) source power: 300 W; and (3) time: 15 minutes. The middle PAEK substrate was treated twice in order to modify both surfaces. Thereafter, a 10% solids solution of polyamic acid in NMP (IMITEC resin 082-081 type 1) was spun cast at 2,000 rpm on each of the surfaces of the two outer PAEK substrates (i.e., one-sided plasma-modified PAEK substrates) until drying (step 810). Subsequently, the resin-modified surfaces of the two outer PAEK substrates were annealed in air at 90° C. for approximately 2 to 3 minutes (step 820). A stack was formed by inserting the middle PAEK substrate between the two resin-modified surfaces of the outer PAEK substrates (step 830), and holding the stack together under a vacuum at approximately 190° C. and 250 psi for 10 minutes and 230° C. and 250 psi for another 30 minutes to cure the adhesive resin (step 840). Upon curing, the three PAEK substrates were strongly bonded, and the adhesive showed excellent solvent resistance.

As will be recognized by those skilled in the art, the innovative concepts described in the present application can be modified and varied over a wide range of applications. Accordingly, the scope of patented subject matter should not be limited to any of the specific exemplary teachings discussed, but is instead defined by the following claims.

We claim:

1. A method for fabricating a microfluidic device, comprising:
   heating a substrate composed of a glassy uncrystallized polyaryl-ether-ketone (PAEK) material from below the glass transition temperature of the PAEK material to at least a temperature sufficient to produce rapid crystallization of the PAEK material;
   embossing said PAEK substrate while the temperature of said PAEK substrate is between the glass transition temperature of the PAEK material and the temperature sufficient to produce rapid crystallization of the PAEK material in said heating to form a patterned PAEK crystalline substrate; and
   forming said microfluidic device using said patterned PAEK crystalline substrate and an additional substrate.

2. The method of claim 1, further comprising:
   applying an adhesion enhancement treatment to respective surfaces of said patterned PAEK substrate and said additional substrate.

3. The method of claim 2, further comprising:
   applying a solvent-resistant adhesive to at least one of said adhesion enhancement-treated surfaces to bond said respective surfaces of said patterned PAEK substrate and said additional substrate together.

4. The method of claim 3, wherein said solvent-resistant adhesive is a polyimide-based adhesive.

5. The method of claim 4, wherein said polyimide-based adhesive comprises a N-methyl pyrrolidone (NMP)-based solution containing a mixture of one or more of the following: thermoplastic polyimides, polyamic acids and partially imidized polyamic acids.

6. The method of claim 3, wherein the layer of said solvent-resistant adhesive on said at least one of said adhesion enhancement-treated surfaces has a thickness substantially less than the thickness of said patterned PAEK substrate.

7. The method of claim 6, wherein the thickness of the layer of said solvent-resistant adhesive on said at least one of said adhesion enhancement-treated surfaces is between 0.1 microns and 1 micron.

8. The method of claim 3, wherein said step of applying said solvent-resistant adhesive further comprises:
   pressing said respective surfaces of said patterned PAEK substrate and said additional substrate together under pressure vacuum and heat.

9. The method of claim 3, further comprising the step of:
   bonding a first surface of said patterned PAEK substrate having said solvent-resistant adhesive thereon and a first surface of a third PAEK substrate; and
   bonding a second surface of said third PAEK substrate and a first surface of said additional substrate having said solvent-resistant adhesive thereon.

10. The method of claim 2, wherein said step of applying further comprises:
    plasma-treating said respective surfaces of said patterned PAEK substrate and said additional substrate.

11. The method of claim 2, wherein said step of applying further comprises:
    sulfonating said respective surfaces of said patterned PAEK substrate and said additional substrate.

12. The method of claim 2, wherein said patterned PAEK substrate comprises first and second patterned PAEK substrates, said additional substrate being one of said first and second patterned PAEK substrates.

13. The method of claim 2, wherein said additional substrate is composed of a solvent-resistant material.

* * * * *